(12) United States Patent
Ishikawa et al.

(10) Patent No.: US 6,734,856 B2
(45) Date of Patent: May 11, 2004

(54) LIVING BODY VARIABLE MEASURING APPARATUS EQUIPPED WITH A DISPLAY CAPABLE OF PRESENTING A GRAPHIC REPRESENTATION

(75) Inventors: Toshihiko Ishikawa, Tokyo (JP); Masato Kodama, Tokyo (JP); Masaru Hirouchi, Tachikawa (JP); Kazuhiko Sakata, Kurihashi-Machi (JP)

(73) Assignee: Tanita Corporation, Tokyo (JP)

( * ) Notice: Subject to any disclaimer, the term of this patent is extended or adjusted under 35 U.S.C. 154(b) by 406 days.

(21) Appl. No.: 09/768,234

(22) Filed: Jan. 25, 2001

(65) Prior Publication Data

US 2001/0050683 A1 Dec. 13, 2001

(30) Foreign Application Priority Data

Jan. 28, 2000 (JP) .................................. 2000-020712

(51) Int. Cl.⁷ .............................................. G06T 11/20
(52) U.S. Cl. ....................................... 345/440; 600/300
(58) Field of Search ................... 345/440–443; 600/300, 301

(56) References Cited

U.S. PATENT DOCUMENTS

| | | | | |
|---|---|---|---|---|
| 4,608,994 A | | 9/1986 | Ozawa et al. | |
| 5,333,244 A | * | 7/1994 | Harashima | 345/419 |
| 5,817,031 A | * | 10/1998 | Masuo et al. | 600/547 |
| 6,354,996 B1 | * | 3/2002 | Drinan et al. | 600/300 |
| 6,516,221 B1 | * | 2/2003 | Hirouchi et al. | 600/547 |
| 6,539,310 B2 | * | 3/2003 | Shimomura | 702/19 |

FOREIGN PATENT DOCUMENTS

| | | |
|---|---|---|
| EP | 1095613 A1 | 5/2001 |
| JP | 6-78827 | 3/1994 |
| JP | 10-192258 | 7/1998 |
| JP | 2998598 | 11/1999 |
| JP | 2000-23935 | 1/2000 |
| WO | WO 99/52425 | 10/1999 |

* cited by examiner

Primary Examiner—Mark Zimmerman
Assistant Examiner—Huedung X. Cao
(74) Attorney, Agent, or Firm—McDermott, Will & Emery

(57) ABSTRACT

Disclosed is an improved living body variable measuring apparatus equipped with a display capable of presenting a time-related graphic representation. The graphic representation is composed of crosswise arrangement of rectangles relative to abscissa and ordinate representing time and measured quantity respectively. Each time-related column has a selected rectangle representing the quantity of a measured living body variable. The horizontal time-related arrangement of narrow rectangles facilitates survey of graphic representation. The living body variable measuring apparatus permits the user to select desired data among those measured for record, preventing so selected data from invading locations allotted to others' data and vice versa.

6 Claims, 14 Drawing Sheets

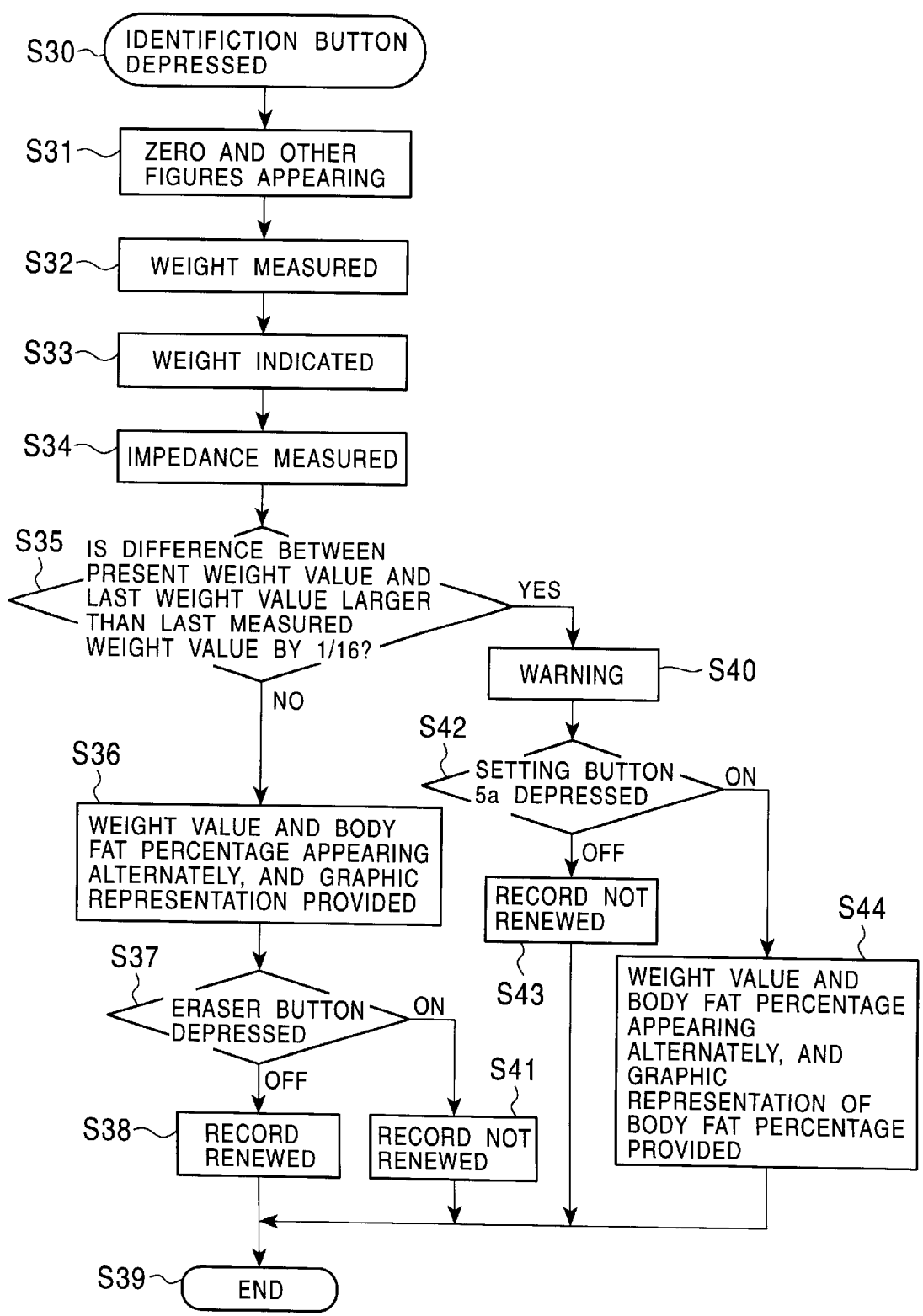

LIVING BODY VARIABLE MEASURING APPARATUS EQUIPPED WITH A DISPLAY CAPABLE OF PRESENTING A GRAPHIC REPRESENTATION

BACKGROUND OF THE INVENTION

1. Field of the Invention

The present invention relates to a living body variable measuring apparatus for measuring different variables characteristic of a living body such as a body fat percentage and other useful pieces of information for health maintenance, and more particularly such a living body variables measuring apparatus capable of presenting graphic representations of measured data.

2. Prior Art

One example of such living body variable measuring apparatus is a body fat gauge. In the body fat gauge a bioelectrical impedance is measured to estimate from the so measured bioelectric impedance a body fat percentage, which is supposed to be one indication for adult sicknesses. A variety of body fat gauges have been proposed and actually used. One of such body fat gauges has display means equipped therewith, automatically indicating a series of body fat percentage each selected among those measured each day in the form of bar chart. This facilitates the recognizing of the dieting result, making it unnecessary for the user to record the body fat percentage at each measurement.

When no measurement is made, a blank appears in the bar chart. Assuming that measurement is not made every day, the bar chart will have a number of blanks at irregular occurrence, thereby making it difficult more or less to realize how one has been dieting one's way down.

A long-termed record of body fat percentage is normally required as the dieting is likely to be continued an elongated length of time. From the point of designing and economical view, however, the area to be occupied by the display is limited in the body fat gauge. As a compromise one body fat percentage is selected among those measured each day to be recorded, as mentioned above. The "single record per day", therefore, cannot meet the user's demand for watching how the body fat percentage varies in a day.

Also disadvantageously, a body fat gauge which permits two or more people to record their body fat percentage in the form of bar charts is apt to allow the user to record his body fat percentage in a wrong location which is allotted to another user.

One object of the present invention, therefore, is to provide a living body variables measuring apparatus equipped with a display capable of presenting a graphic representation, which living body variables measuring apparatus is free of disadvantages such as described above, facilitating a good understanding of the presented graphic representation; providing the advantage of versatile records of measurement; and preventing one's record from being interfered by others' records.

SUMMARY OF THE INVENTION

To attain this object a living body variable measuring apparatus equipped with a display capable of presenting a graphic representation is improved according to the present invention in that the graphic representation is composed of crosswise arrangement of rectangles relative to abscissa and ordinate representing time and measured quantity respectively, thus permitting each rectangle to represent a quantity measured at a selected time. This arrangement has the advantage of facilitating the grasping of the presented graphic representation even though blanks appear in the graph thanks to the limiting of the required pieces of information to specific narrow areas.

Each rectangle has relatively long horizontal sides and relatively short vertical sides. This configuration facilitates the lateral sweeping of the line of sight to survey how the time-related variation is like.

Rectangles may have different shapes and/or sizes and/or colors for distinctive lengths of time. Different groups of information can be allotted to rectangles distinctively distinguishable from others in terms of shape, size and/or color, thus facilitating the understanding of presented graphic representations still more.

The rectangular presentation beyond the permitted range of measured quantity may be different from the rectangular presentation within the permitted range of measured quantity in appearance. This assists a quick understanding of graphic representations.

The display may show how much a mark-to-mark space or division indicates when switching from the minimum range of measurement to the maximum range of measurement or inversely in the scale. A good understanding of presented graphic representation in terms of what quantity is indicated by mark-to-mark space or division at the first glance.

A living body variable measuring apparatus equipped with a display capable of presenting a graphic representation is improved according to the present invention in that it includes a decision making unit, thereby permitting the user to make a required decision in terms of whether the measured quantity should be recorded or not. This assures that the graph be composed exclusively of the records which the user makes, allowing no blanks to appear in the graph. Also advantageously, the records selected by the user can be held exclusively, thus preventing the recording of the result of such undesired measurement as erroneously made by referring to others' personal particulars. No interference of others' records are assured equally.

In case of two or more people being permitted to record their measurement results the living body variables measuring apparatus may further comprise a warning unit which informs the user of a wrong measurement if made, by referring to others' particulars already registered. This assures no interference of others' records.

A living body variable measuring apparatus equipped with a display capable of presenting a graphic representation is improved according to the present invention in that it includes a data-acquirement time setting unit, thereby permitting the user to selectively determine at what time the required measurement may be made. This permits the user to make a required measurement when he presumes to be convenient, thereby contributing reduction of blanks in the graph, and at the same time, minimizing the possibility of allowing others' records to invade in the location allotted to the user's record or vice versa thanks to the time-division recording allotted to individuals.

In the graphic representation different lengths of time allotted to different measurements may be distinguishable in color.

Other objects and advantages of the present invention will be understood from some preferred embodiments of the present invention, which are shown in the accompanying drawings:

FIG. 11 is a flow chart describing what sequential actions are taken in measurement;

DESCRIPTION OF PREFERRED EMBODIMENTS

Figure 1:
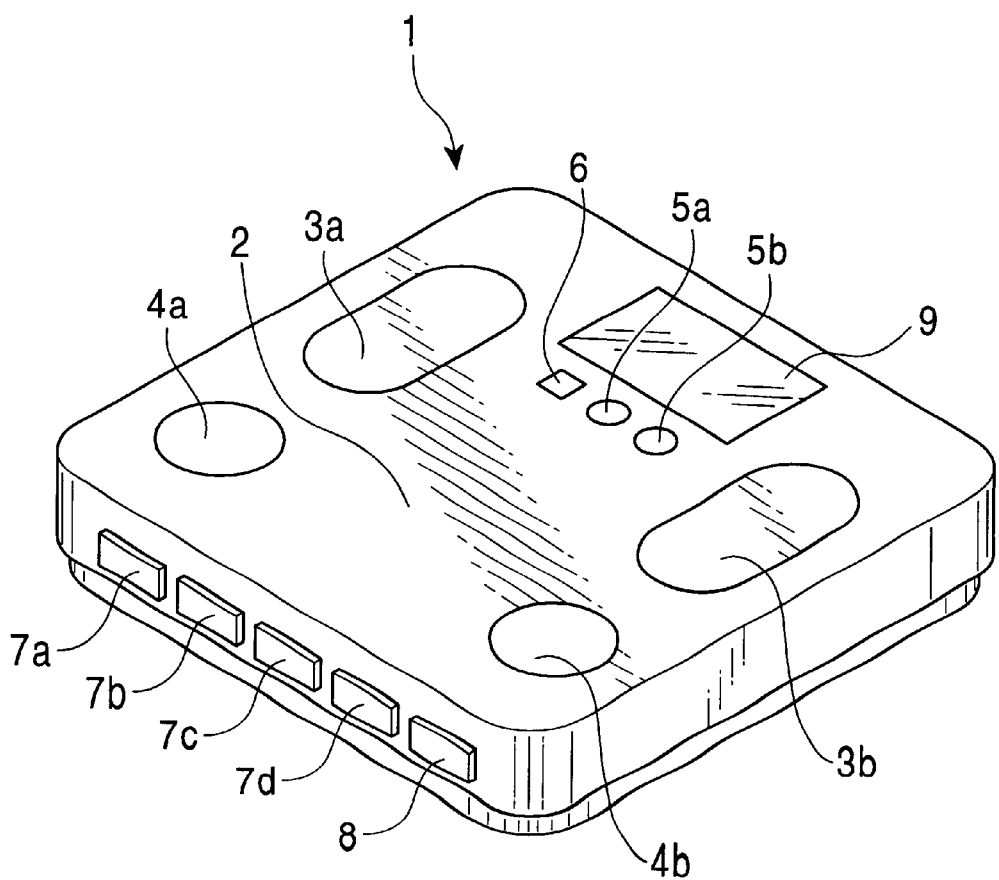
FIG. 1 is a perspective view of a body fat gauge having the function of providing graphic representations.
Figure 2:
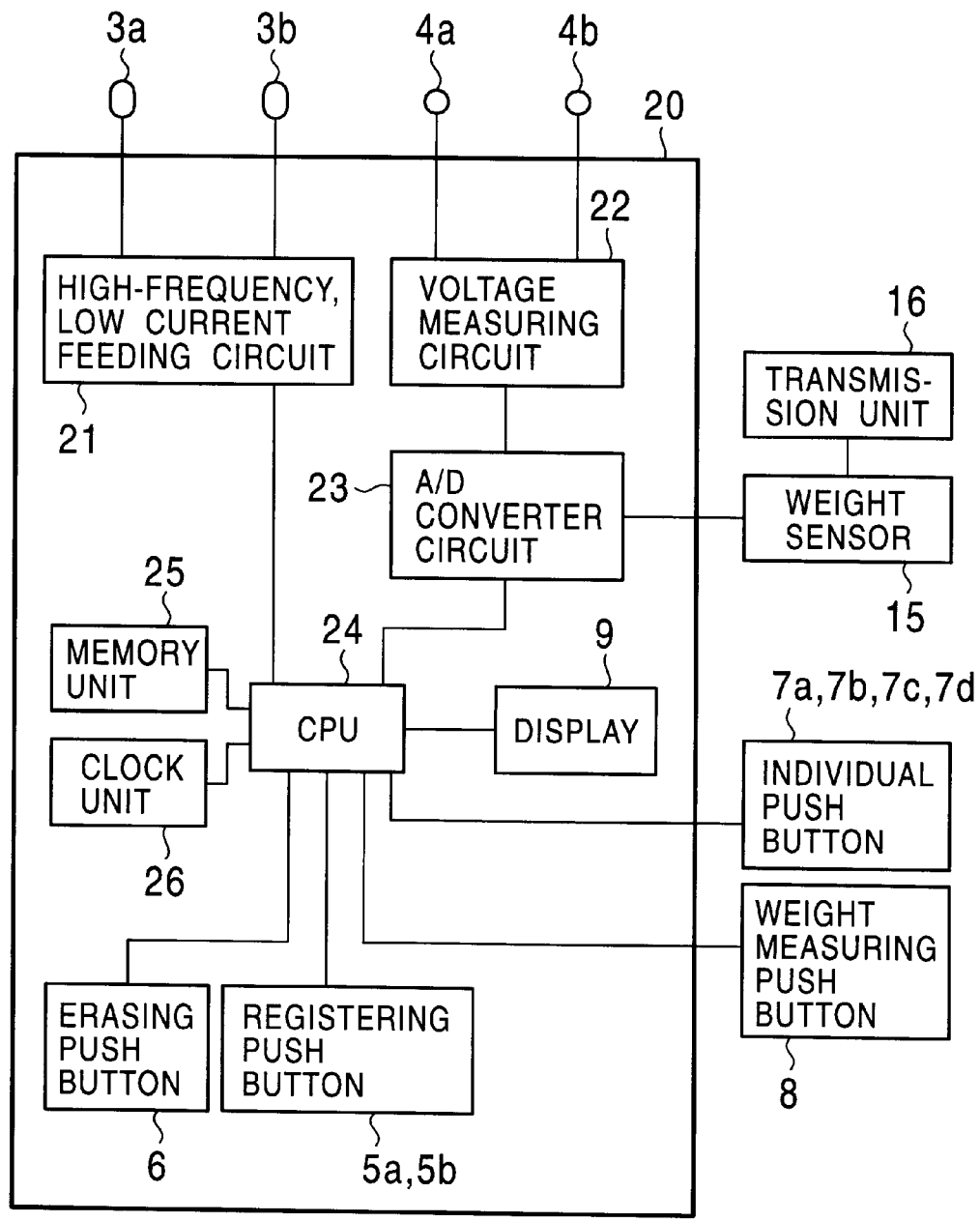
FIG. 2 is a wiring diagram of the electric circuit contained in the body fat gauge.

Referring to FIGS. 1 and 2, a body fat gauge 1 according to a first embodiment has on its weight scale base 2 two current feeding electrodes 3a and 3b for making an electric current to flow in a living body; two voltage detecting electrodes 4a and 4b for use in measuring the voltage appearing between two selected points in the body; two registering push buttons 5a and 5b for registering individual particulars and setting given lengths of time; an erasing push button 6 for erasing undesired records; individual push buttons 7a, 7b, 7c and 7d for relating a required measurement with the individual particulars; a weight measuring push button 8 for measuring individual weights; and a display 9 for showing the individual particulars registered and the results of measurement. The body fat gauge 1 has a weight sensor 15 responsive to the weight load for converting the same to electric signals, a transmission unit 16 for transmitting the weight to the weight sensor 15, an electronic circuit board 20 and other parts all built in its casing.

The electronic circuit board 20 comprises a high-frequency, low current feeding circuit 21 for supplying a constant current of high-frequency to the display 9, the erasing push button 6, the registering push buttons 5a and 5b and the current feeding electrodes 3a and 3b, a voltage measuring circuit 22 for measuring the voltage appearing between the opposite voltage detecting electrodes 4a and 4b, an analog-to-digital converter circuit 23 for converting analog signals both from the voltage measuring circuit 22 and from the weight sensor 15, a memory unit 25 for storing individual particulars and measured quantities, a clock unit 26 for setting lengths of time as required and a CPU 24 for effecting required arithmetic operations and controls for determining the body fat percentage on the basis of so determined bioelectrical impedance and weights.

The current feeding electrodes 3a and 3b, the voltage detecting electrodes 4a and 4b, the weight sensor 15, the individual push buttons 7a, 7b, 7c and 7d, and the weight push button 8 are connected to selected terminals in the electronic circuit board 20.

Figure 3:
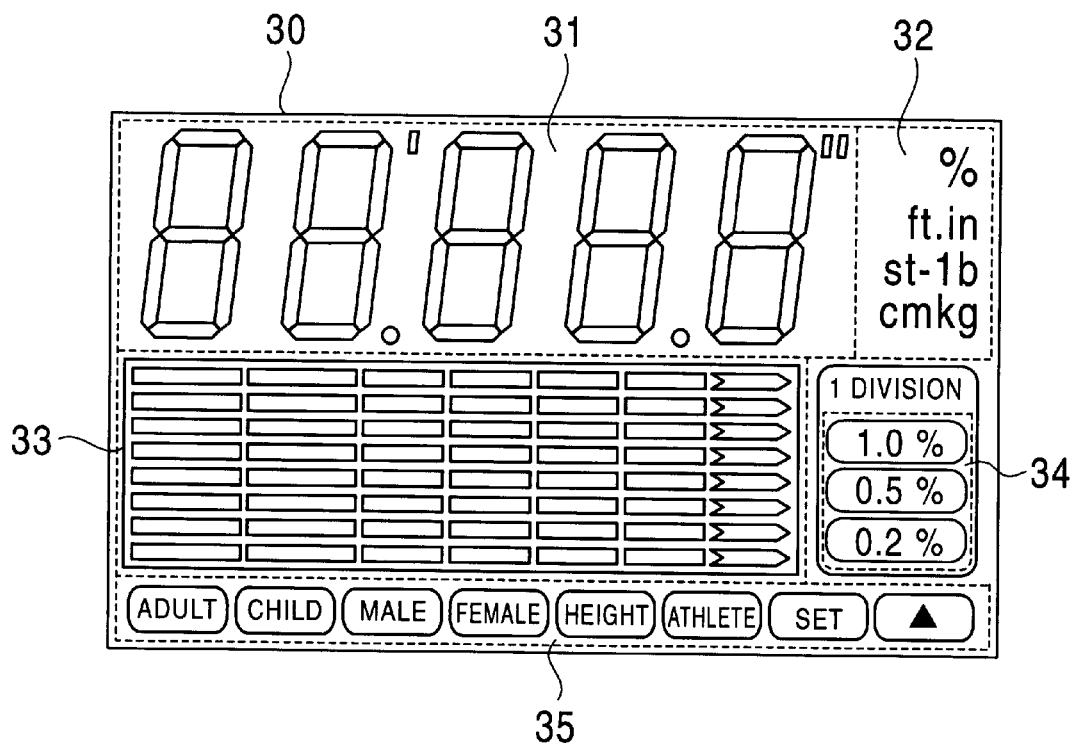
FIG. 3 illustrates the display of the body fat gauge capable of providing a graphic representation.
Figure 4:
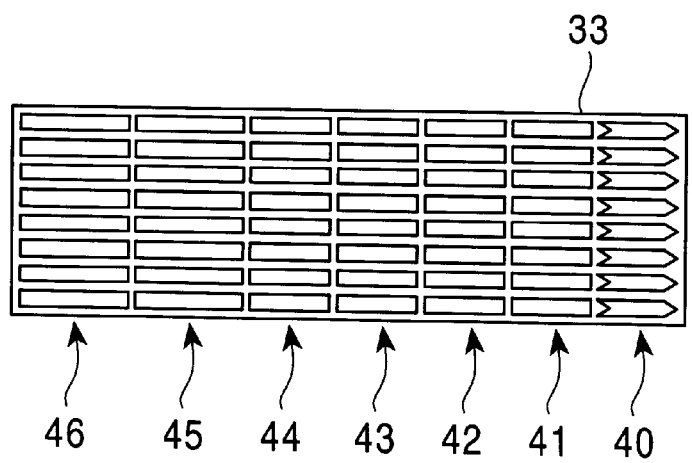
FIG. 4 illustrates the section of the display, on which section a required graphic representation is given.

Referring to FIGS. 3 and 4, the display area 30 shows a numerical value indicating sub-section 31 and a unit indicating sub-section 32 in its upper part, a graphic representation sub-section 33 and mark-to-mark quantity indicating sub-section 34 in its middle part, and an individual particulars indicating section 35 in its bottom part.

In the numerical value indicating sub-section 31 there appear individual particulars recorded, time set for different purposes, results of measurement and such like when demanded. The unit indicating sub-section 32 shows the units of different measurements, the numerical value each measurements being given in the numerical value indicating sub-section 31.

The graphic representation sub-section 33 is composed of crosswise arrangement of rectangles, indicating time (abscissa) and measured quantity (ordinate). The measured result at a selected time is indicated by allowing a selected single rectangle to flash. Seven rectangle abscissas are arranged in horizontal direction whereas eight rectangle ordinates are arranged in vertical direction. The far right column 40 indicates data measured today. The second, third, fourth and fifth columns 41 to 44 from the right indicate data measured each week as follows: the second column 41 indicates the mean value of data taken each of the seven previous days counted from today; the third column 42 indicates the mean value of data taken each day of the previous second week; the fourth column 43 indicates the mean value of data taken each day of the previous third week; and finally the fifth column 44 indicates the mean value of data taken each day of the previous fourth week. The far left column 46 and the second column 45 from the left indicate monthly data. Specifically the second column 45 indicates the mean value of data taken each of thirty days before the last day of the previous one month-long period beginning with today, and the far left column 46 indicates the mean value of data taken each of thirty days before the last day of the previous two month-long period beginning with today. It should be noted that: the far right column 40 is composed of arrow-like rectangles; the second, third, fourth and fifth columns 41, 42, 43 and 44 from the right are composed of relatively short rectangles; and the second and far left columns 45 and 46 are composed of relatively long rectangles. The lateral time-related arrangement of rectangles of different shape and size makes it easy to distinguish such columns in terms of which rectangles are allotted to which time set for measurement. Such distinction may be provided by showing selected groups of columns in different colors. The far right column 40, the second, third, fourth and fifth columns 41, 42, 43 and 44 from the right in group and the second column 45 from the left and the far left column 46 may have different-colored backgrounds.

In case that the maximum to minimum values of body fat percentage recorded previously ranges from 0 to 1.4%, and then, the mark-to-mark space or division is automatically changed to 0.2%; in case that the maximum to minimum values of body fat percentage recorded previously ranges from 1.4% to 3.5%, and then, the division is automatically changed to 0.5%; and in case that the maximum to minimum values recorded previously increases beyond 3.5%, and then, the division is automatically changed to 1.0%. When the quantity measured increases beyond the maximum limit of indication range, i.e. 7%, the top or bottom rectangle of the column is made to flash.

The mark-to-mark space or division in the graphic representation sub-section 33 is automatically selected for indication. The individual particulars indicating section 35 show personal particulars for reference in measurement.

Figure 5:
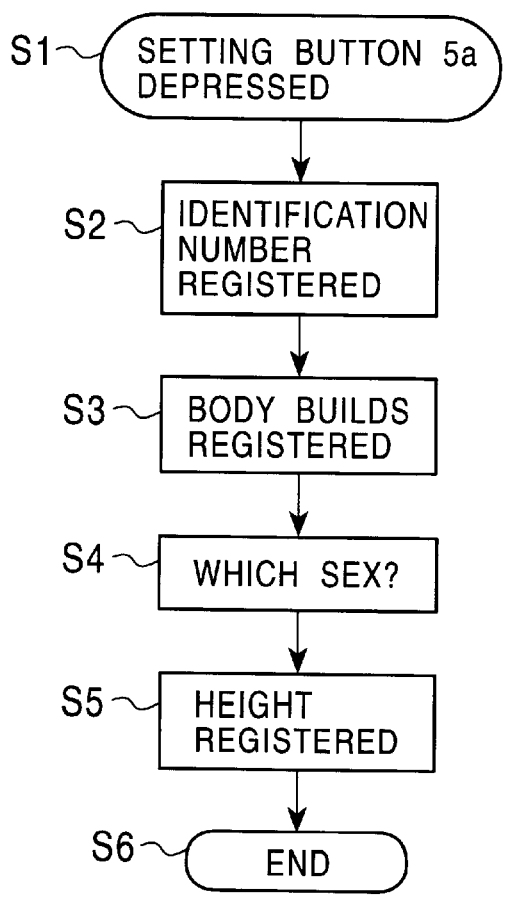
FIG. 5 is a flow chart describing how individual particulars can be recorded.

Referring to FIG. 5, a series of actions taken for setting and recording individual particulars in the body fat gauge are described. A user must follow these steps if the user uses the body fat gauge for the first time. Also, the user must follow these steps if he wants to renew some selected individual data once recorded. At the outset the user depresses the registering push button 5a (STEP S1), going to the inputting mode of identification number (STEP S2). In this mode a given number appears in the numerical value indicating sub-section 31 to be changed every time when the registering push button 5b is depressed, thereby permitting the user to select a desired number for identification. The identification number thus selected can be registered by depressing the registering push button 5a.

Next, the user proceeds to the mode of inputting body builds (STEP S3). In this mode the words, "adult", "child" and "athlete" appear one after another in the individual particulars indicating section 35 every time the registering push button 5b is depressed, thus permitting the user to select a desired one among those words. The user can record the so selected one by depressing the registering push button 5a.

Next, the user proceeds to the mode of selecting which sex (STEP S4). In this mode the words, "male" and "female" appear in the order described in the individual particulars indicating section 35, thus permitting the user to select which sex. The user can record the so selected sex by depressing the registering push button 5a.

Next, the user proceeds to the mode of inputting the height (STEP S5). In this mode a predetermined height appears in the numerical value indicating sub-section 31 to be changed every time the registering push button 5b is depressed, thereby permitting the user to select a desired number as the user's height. The height thus selected can be registered by depressing the registering push button 5a, thus finishing registration of individual data (STEP S6).

When all individual data are inputted for registration, the user is informed of which push button 5a or 5b is selected for subsequent depression in the individual particulars indicating section 35, thus making it unnecessary to refer to the operation guidance.

Figure 6:
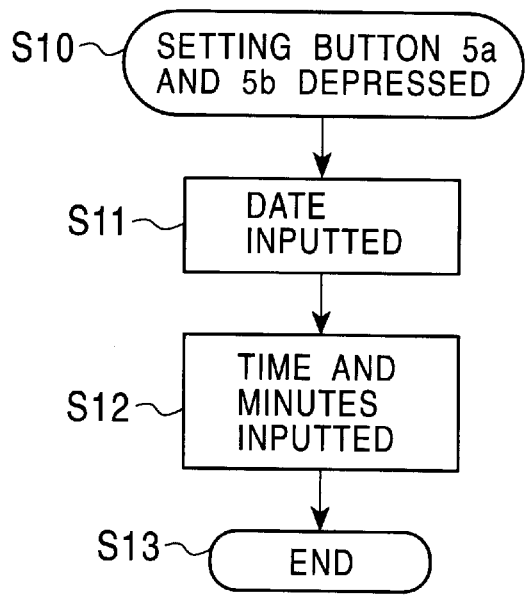
FIG. 6 is a flow chart describing how time and day can be set for measurements of body fat percentage.

Referring to FIG. 6, some sequential steps for setting date in the body fat gauge are described. First, the user depresses the registering push buttons 5a and 5b simultaneously (STEP S10) to proceed to the mode of inputting the date (STEP S1). In this mode the far left figure appearing in the numerical value indicating sub-section 31 is changed every time the registering push button 5b is depressed, thereby permitting the user to select the least significant digit of the dominical year. The figure thus selected is registered by depressing the registering push button 5a. Next, the second figure from the left is changed every time the registering push button 5b is depressed, and likewise, the third figure is changed, permitting the user to select the number representing the month. The number thus selected is registered by depressing the registering push button 5a.

Finally, the fourth and fifth figures from the left are changed as desired, thereby permitting the user to select the number representing the day. The number thus selected is registered by depressing the registering push button 5a.

Next, the user proceeds to the mode of inputting time and minutes (STEP S12). In this mode the second and third figures from the left side of the numerical value indicating sub-section 31 are changed every time the registering push button 5b is depressed, thereby permitting the user to select the number representing time. The number thus selected is registered by depressing the registering push button 5a. Then, the fourth and fifth numbers from the left are changed until the number representing minutes appear. The number thus selected is registered by depressing the registering push button 5a.

Figure 7:
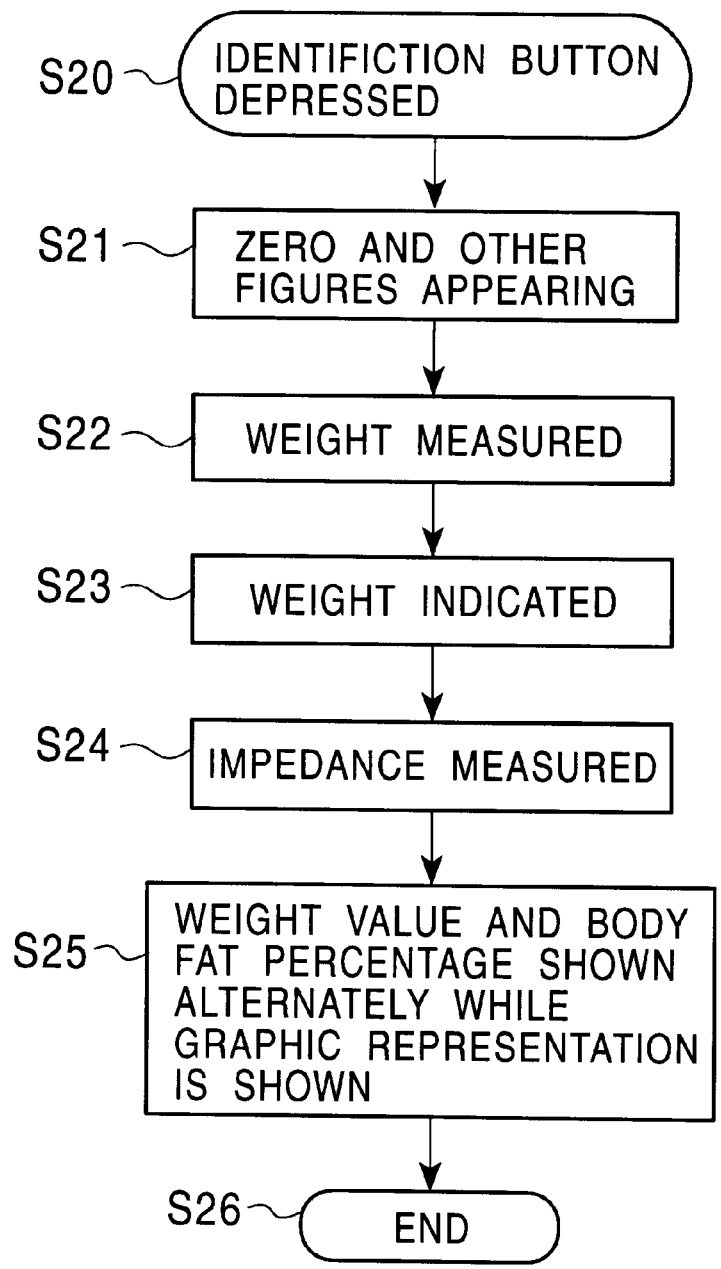
FIG. 7 is a flow chart describing what sequential actions are taken in determining the body fat percentage.

Referring to FIG. 7, sequential steps for measuring the body fat percentage are described. First, the user depresses the identification button (STEP S20) to retrieve the personal particulars in terms of identification number. At the outset zeros appear in the numerical value indicating sub-section 31, and the individual particulars appear in the individual particulars indicating section 35 (STEP S21).

The user stands on the weight scale base 2 to determine the user's weight (STEP S22), and then, the so determined weight is given in the numerical value indicating sub-section 31 (STEP S23). Then, the bioelectrical impedance is measured (STEP S24). The weight value and the body fat percentage are shown alternately while the graphic representation is shown without intermission. As in the prior art, the measured data are automatically recorded in the memory 25. If several measurements are effected in a day, only the last measurement is recorded, and the measurement is finished (STEP S26).

One example of the presentation at STEP S25 is shown in FIGS. (8a) and (8b). Specifically the numerical value indicating sub-section 31 shows the body fat percentage, and the unit indicating sub-section 32 shows the particular unit, % for the presented body fat percentage in FIG. 8(a). The graphic representation sub-section 33 gives a graphic representation showing how the body fat percentage has been varying with time. The flashing rectangle 36 indicates that the measured body fat percentage is so large in value that it is beyond the indication-permissible range. The mark-to-mark quantity indicating sub-section 34 shows 1.0%, indicating that the rectangle division is equal to 1.0%. The individual particulars indicating section 35 indicates that the user is registered as "adult" and "female". In FIG. 8(b) the numerical value indicating sub-section 31 shows the weight value, and the unit indicating sub-section 32 shows the particular unit "kg" of the presented weight value. The other indicating sub-sections show same information as in FIG. 8(a). The presentations of FIG. 8(a) and FIG. 8(b) appear alternately.

Figure 8A:
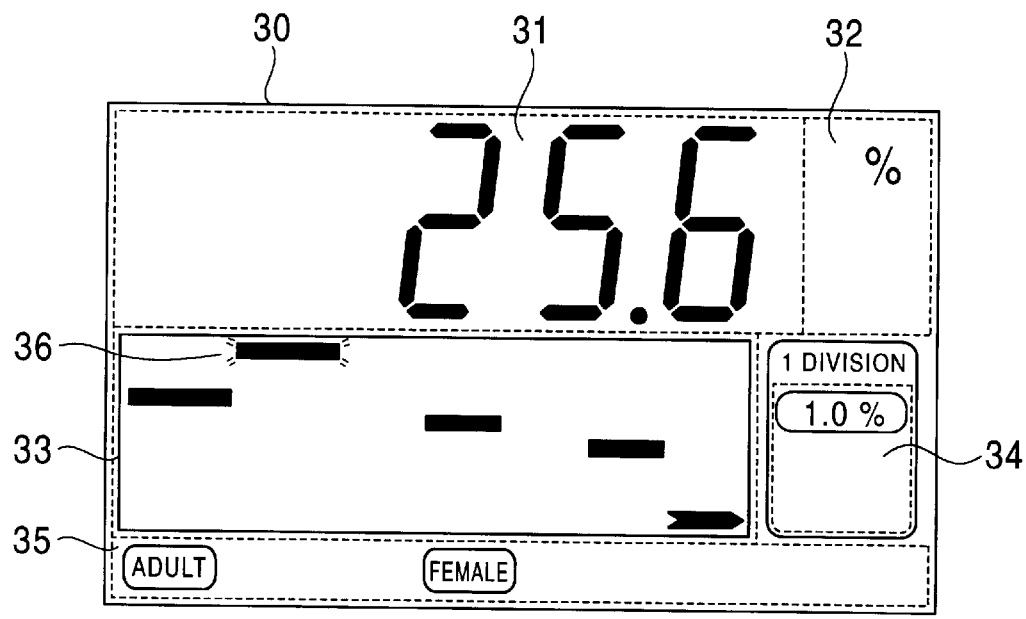
FIGS. 8a and 8b illustrate what are like in the display.
Figure 8B:
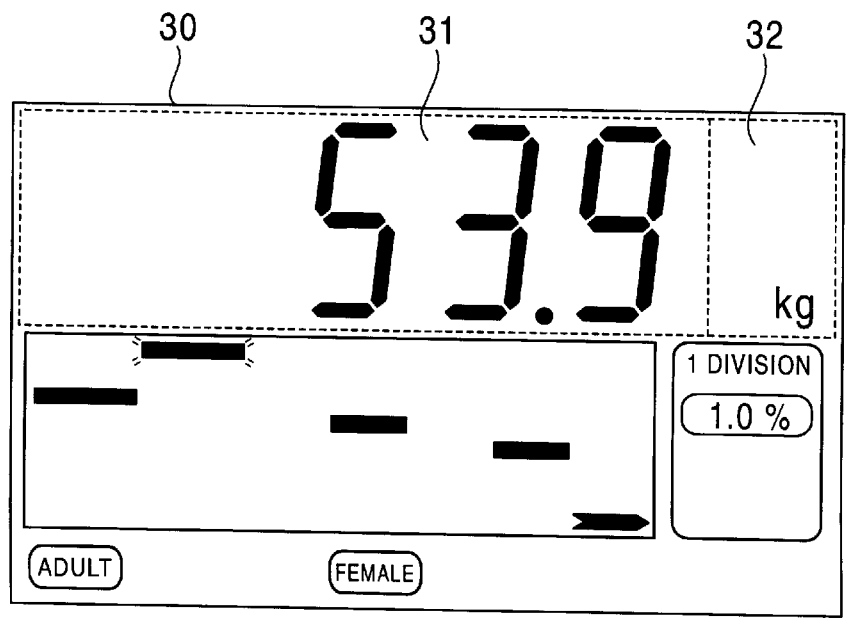

As seen from FIGS. 8(a) and 8(b), each rectangle appearing in the graphic representation sub-section 33 occupies an area much smaller in vertical dimension than the longitudinal bar in the bar graph used in the prior art device, and rectangles arranged at different levels are easy for eyes to follow, not being disturbed by blanks, if any.

Figure 9:
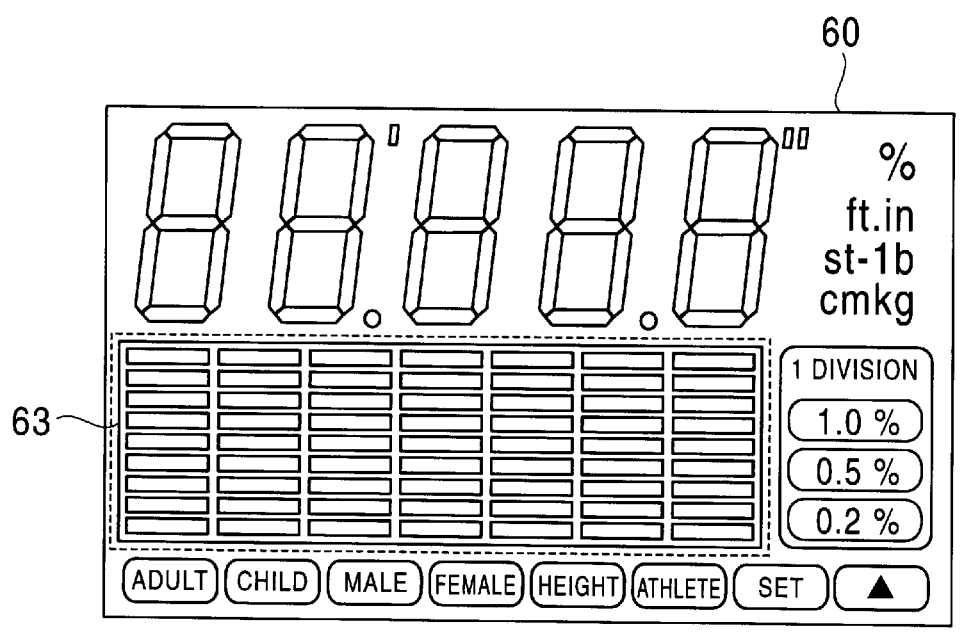
FIG. 9 illustrates another example of display.

Different from the graphic representation domain 33 in FIG. 3, all rectangles in the graphic representation domain 37 are same in shape and size in FIG. 9.

In order to make time-related columns distinguishable from each other the rectangles of each column may be modified as for instance, follows: the rectangles of each column are different in lateral size; the rectangles of each column are different in color; or the background of each column is different in color.

The unit range available is given in response to the switching of the unit ranges spanning from the minimum to maximum measurement range, thus permitting the user to understand quickly what unit is now used at the sight of the right side of the display.

Figure 10:
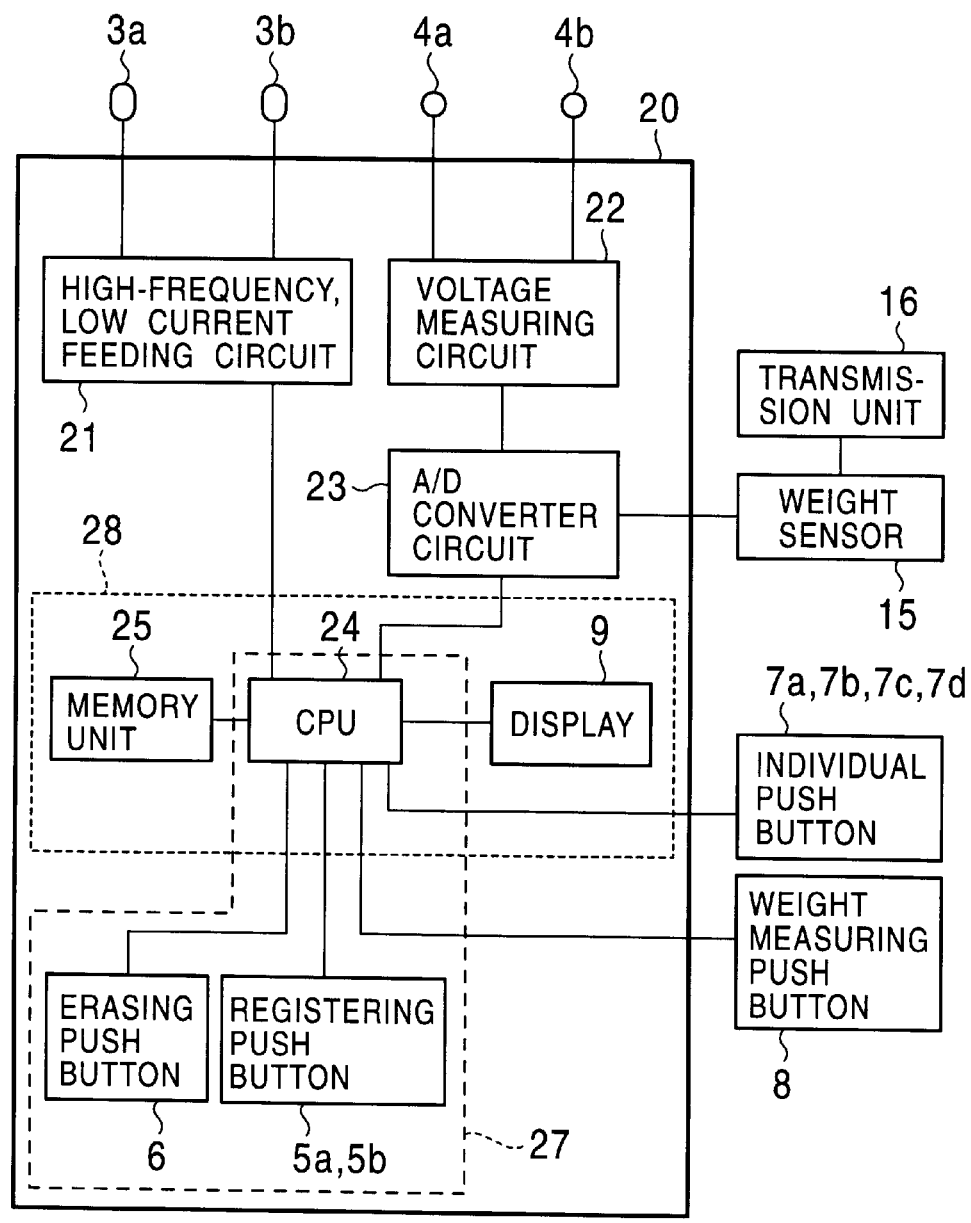
FIG. 10 illustrates a wiring diagram of the electric circuit contained in the body fat gauge.

Now, the second embodiment is described by referring to some drawings. The whole structure looks like the one of FIG. 1, and has the electric circuit of FIG. 10, which may be provided by modifying the electric circuit of FIG. 2 by removing the clock unit 26 and by adding an acquirement decision making unit 27 for making a decision in terms of whether the measured data is registered or not, and a warning unit 28 for informing the user of the measurement being made relative to wrong personal particulars. As for the acquirement decision making unit 27 it comprises two different combinations: one is a combination of an eraser button 6 for generating a "No Acquirement" representative signal and the part of CPU 24 functioning to make a required decision in terms of whether the measured data is recorded or not depending on the presence or absence of the "No Acquirement" representative signal from the eraser button 6, executing a required processing accordingly whereas the other is a combination of a registering push button 5a or 5b for generating an "Acquirement Permitted" representative signal and the part of CPU 24 functioning to make a required decision in terms of whether the measured data is recorded or not depending on the presence or absence of the "Acquirement Permitted" representative signal from the registering push button 5a or 5b, executing a required processing accordingly. As for the warning unit 28 it comprises a memory 25 for storing a certain measured data as a reference, a warning display 9 and the part of CPU 24 functioning to make a decision in terms of whether the user is warned or not, executing a required processing accordingly. The remaining of the whole structure is same as the first embodiment, and therefore, further description is omitted.

As for the presentation domain of the display 9 it has the same structure as the display area 30 of FIG. 3, but the contents of the graphic representation domain 33 are different from those in the first embodiment. Referring to FIG. 4 again, the far right column 40 indicates data measured this time. The second column 41 from the right indicates the mean value of the last and six preceding data; the third, fourth and fifth columns 42 to 44 from the right have indications of the mean values of previous seven data sequentially shifted leftward every time a new average appears in the second column 41. The second column 45 from the left shows the mean value of the four mean values shifted to the second column 45. The far left column 46 indicates the mean value of the four mean values shifted to the far left column 46. The remaining is same as the first embodiment, and therefore, further description is omitted.

Referring to FIG. 11, sequential steps for measuring the body fat percentage are described below. The manner in which the individual particulars are registered is same as in the first embodiment, and therefore reference is made to the relevant description. The measurement begins with depression of the identification button (STEP S30). Then, zeros appear in the numerical value indicating sub-section 31, and the particulars of the user appear in the individual particulars indicating section 35 (STEP S31).

The user stands on the weight scale base 2 to determine the user's weight (STEP S32), and then, the so determined weight is given in the numerical value indicating sub-section 31 (STEP S33). Then, the bioelectrical impedance is measured (STEP S34). The CPU 24 compares the so determined weight value with the last weight value already registered (STEP S35). If the difference therebetween is found to be larger than the last measured weight value by one sixteenth thereof, the proceeding goes to STEP S40, thus warning the user of the possibility of the measurement being based on wrong personal particulars. If not, the proceeding goes to STEP S36.

Specifically at STEP S40 the letters, "No" and the identification number appear alternately as warning indication, which is given in flashing condition in the numerical value indicating sub-section 31, and at the same time, the mark, "x" appears in the graphic representation domain 33. If the difference therebetween is found to be smaller than the last measured weight value by one sixteenth thereof, the proceeding goes to STEP S36, where the weight value and the body fat percentage appear alternately, and at the same time, the graphic representation is provided in the numerical value indicating sub-section 31.

While the measurement results are shown at STEP S36, the eraser button 6 is depressed (STEP S37), thus finishing without registering the last measurement data in the memory 25 (STEP S39). If the eraser button 6 is not depressed (STEP S37), the record is renewed by allowing the last measurement data to be stored in the memory 25 (STEP S38). Thus, the proceeding is finished (STEP S39).

If the registering push button 5a is not depressed while warning at STEP S40 (STEP S42), the proceeding ends (STEP S42) without recording the last measurement data in the memory 25 (STEP S39). If the registering push button 5a is depressed (STEP S42), the weight value and the body fat percentage appear alternately, and at the same time, the graphic representation of the body fat percentage is provided in the numerical value indicating sub-section 31. The proceeding ends (STEP S39) with the last measurement data recorded in the memory 25 (STEP S44).

One example of the presentation at STEP S36 is shown in FIG. 12.

Figure 12A:
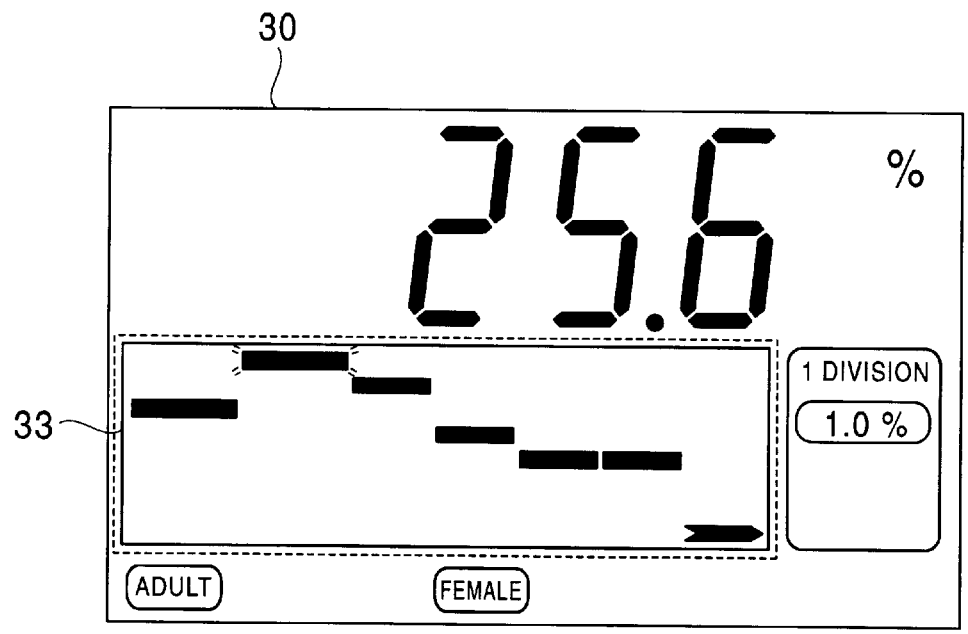
FIGS. 12a and 12b illustrate what are like in the display.
Figure 12B:
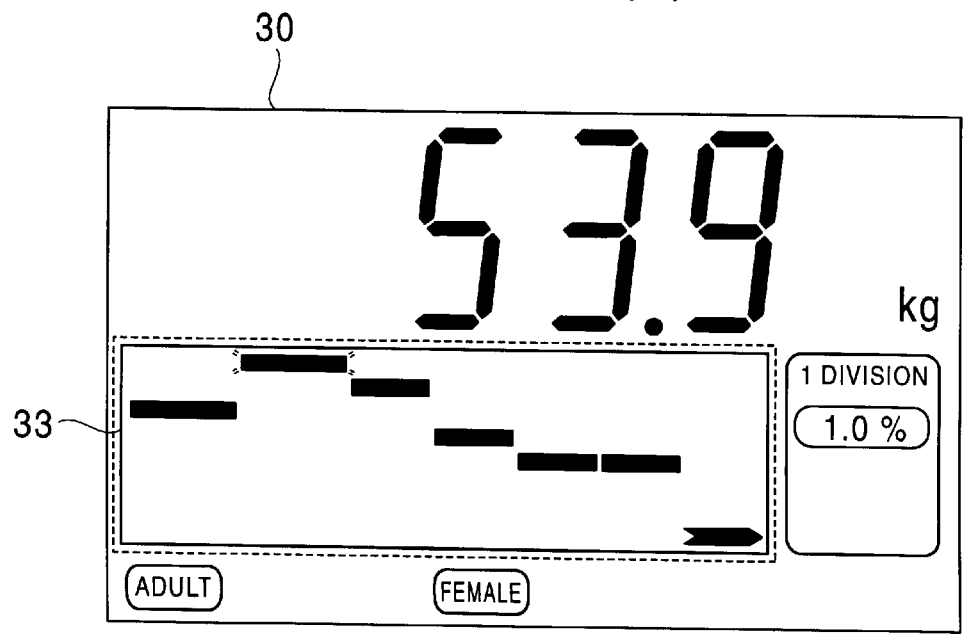

The presentations of FIGS. 12(a) and 12(b) appear alternately. As may be noted, no blanks appear in the graphic representation domain 33; each of the time-related columns has a rectangle representing a measured value. Everything else is same in the first embodiment, and further description, therefore, is omitted.

As may be perceived in the second embodiment, the data, of which acquirement is confirmed by the user at STEPs S37 and S38 in FIG. 11, are given in the form of graph. Thus, no blanks appear in the graphic representation, as seen from FIG. 12.

Assuming that a long period has not passed from the last but one weight measurement to the last weight measurement, it is rare that the difference therebetween is beyond one sixteenth of the last but one weight for one and same person. Stated otherwise, such is not rare if the last but one weight measurement pertaining to one person and the last weight measurement pertaining to another person are compared. The required decision making at STEP S35 in FIG. 11 relies on this most probable incidence. Thus, the user can be informed of wrong measurement made by referring to other personal records at STEP S40. After being warned, the user is permitted to make a final decision in terms of whether the measured data is recorded or not at STEP S42. Thus, there is, in fact, no fear of interfering others' records.

For normal measurements the user is permitted to make a required decision in terms of whether the measured data is acquired or not at STEP S37 and proceed accordingly. Apart from the prior art which permits a single measurement data to be recorded in a day, the selecting and recording of data is left to the user's discretion.

If the eraser button 6 is depressed, the content of the memory cannot be renewed, and if not, the content of the memory can be renewed, as described above. The inverse is permissible, that is, if the eraser button 6 is depressed, the content of the memory can be renewed, and if not, the content of the memory cannot be renewed.

Figure 13:
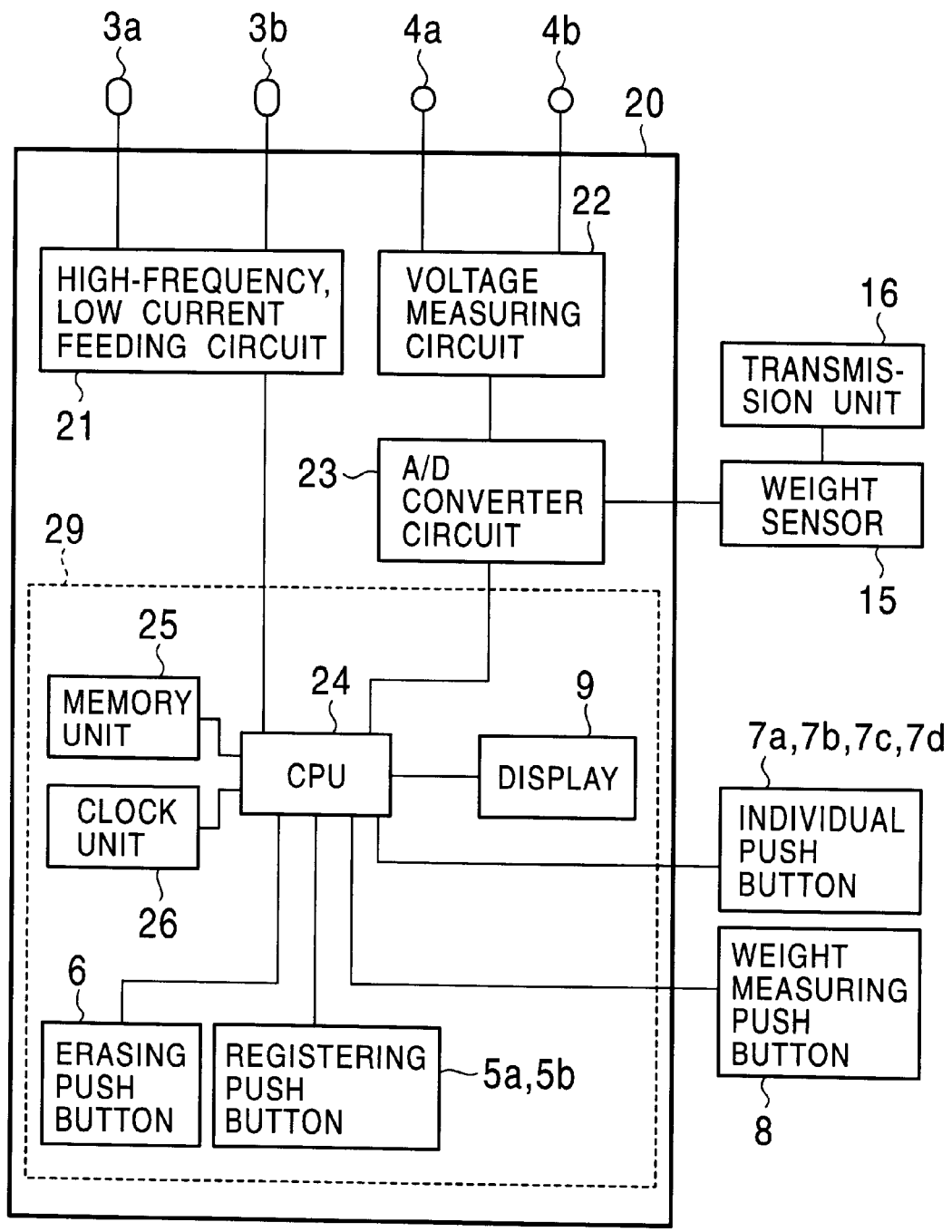
FIG. 13 illustrates a wiring diagram of the electric circuit contained in the body fat gauge.

Now, the third embodiment is described by referring to some drawings. The whole structure looks like the one of FIG. 1, including the electric circuit of FIG. 13, which may be provided by adding to the electric circuit of FIG. 2 acquirement time setting means for setting periods of time for data-acquirement. The acquirement time setting means 29 comprises an eraser button 6 and registering push buttons 5a and 5b for inputting a selected length of time for data-acquirement, a display 9 for showing a variable duration for selection, a memory 25 for storing the data-acquirement period, and a clock 26 for generating clock signals, all of which are connected to the CPU 24 for effecting required operations. The display 9 has a presentation domain 60 as shown in FIG. 9. The remaining parts of the third embodiment are same as the first embodiment, and reference is made to the relevant description.

Figure 16:
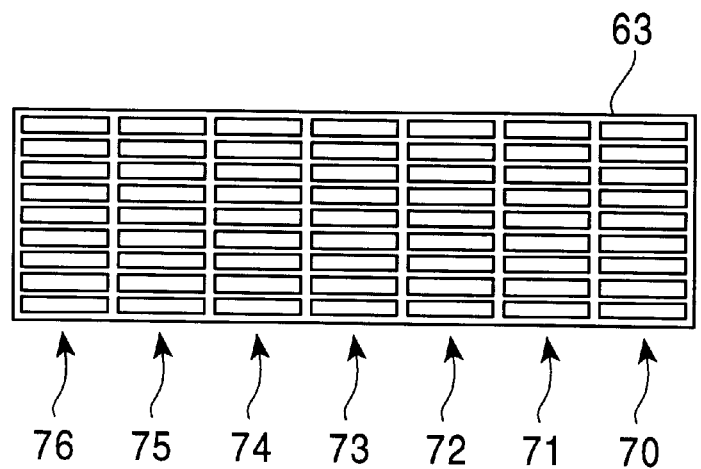
FIG. 16 illustrates the section of the display, on which section a required graphic representation is given.

The presentation domain 60 of the display 9 is described below. Referring to FIG. 16, the graphic representation area 63 shows how data obtained for a series of data-acquirement periods vary. Specifically, the far right column 70 indicates data measured this time. Every time measured data has been acquired, it is shown in the far right column, allowing the previous measured data to be shifted to the second and subsequent columns 71–76 sequentially, thus showing how the body fat percentage has been varying. The remaining parts of the presentation domain is same as the first embodiment, and reference is made to the relevant description.

Now, the manner in which the third embodiment works is described. The recording of personal particulars, the setting of time and the proceeding of measurement are same as in the first embodiment.

Figure 14:
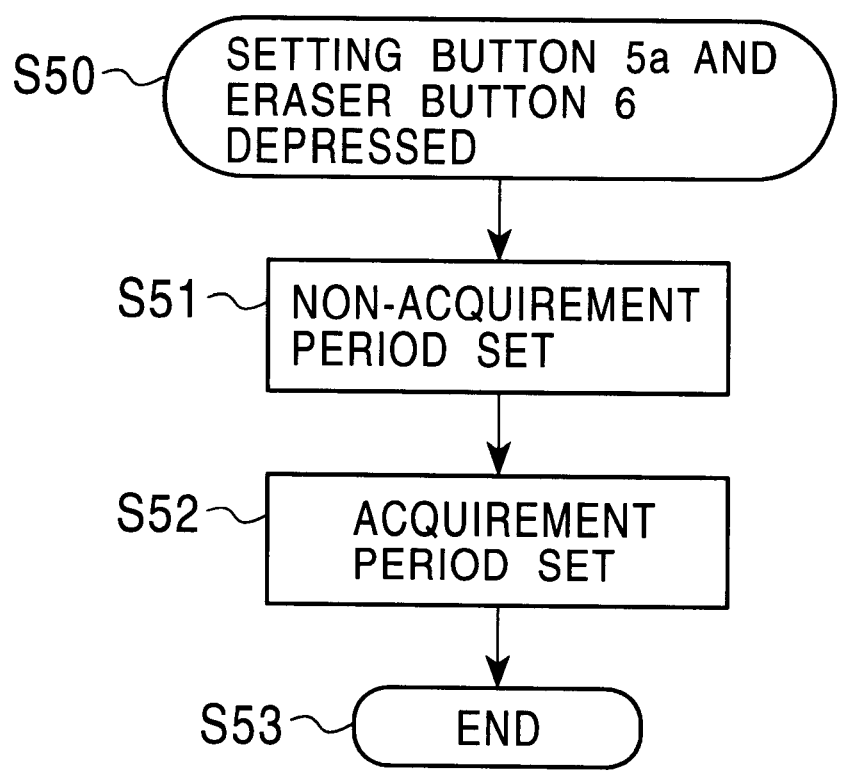
FIG. 14 is a flow chart describing how time can be set for data acquirement and non-data acquirement.
Figure 15:
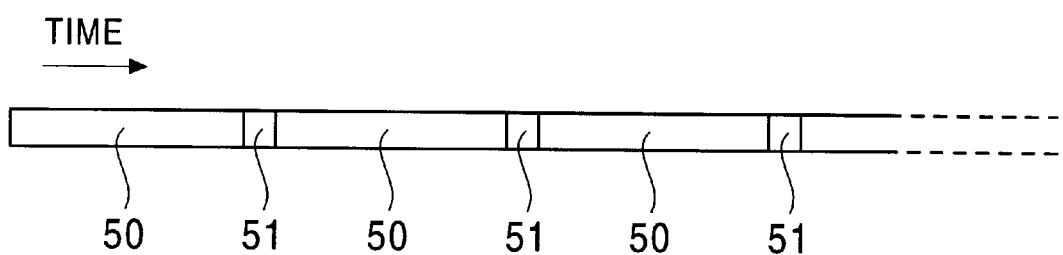
FIG. 15 illustrates a time-related arrangement of durations set for acquirement of body fat percentage.

FIG. 14 shows a series of actions taken for setting periods of time for acquirement of required data, and FIG. 15 illustrates how acquirement periods 51 are distributed. When setting the acquirement period, the registering push button 5a and the eraser button 6 are depressed simultaneously (STEP S50), allowing the proceeding to go to the non-acquirement period setting mode (STEP S51). In this mode a desired non-acquirement period 50 can be set by depressing the registering push buttons 5a and 5b. Specifically depression of the registering push button 5b causes hour and minute to appear in the display 9 for selection, and depression of the registering push button 5a causes the so selected hour and minute to be registered.

Then, the proceeding goes to the acquirement period setting mode (STEP S52). In this mode a desired acquirement period 51 can be set by depressing the registering push buttons 5a and 5b. Specifically depression of the registering push button 5b causes hour and minute to appear in the display 9 for selection, and depression of the registering push button 5a causes the so selected hour and minute to be registered. Thus, the time setting and recording is finished.

Figure 17A:
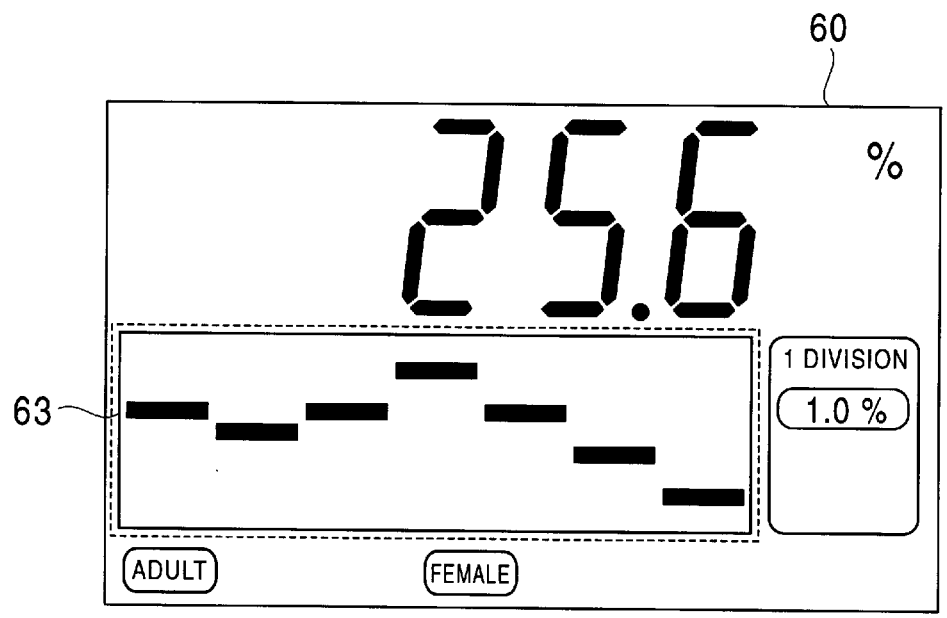
FIGS. 17a and 17b illustrate what are like in the display.
Figure 17B:
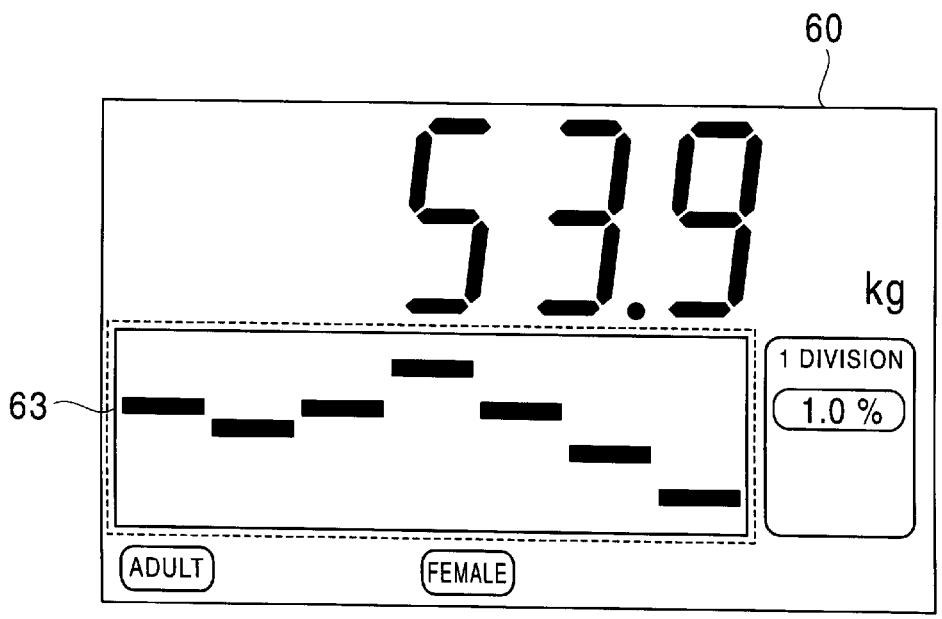

FIG. 17 shows one example of presentation domain of the display in the third embodiment. The presentations of FIGS. 17(a) and 17(b) appear alternately. As shown, no blanks appear in the graphic representation of body fat percentage 63, as is the case with the second embodiment; each and every time-related column includes a measured value of rectangle, and is free of any blank showing absence of measured data. Everything is same as in the first embodiment except for the graphic representation 63, and further description is omitted.

The alternate time-related arrangement of acquirement periods and non-acquirement periods enables the user to have desired measurements in pace with his life-way. No blanks appear in the graphic representation. This is the same with the bar graphic representation.

The arbitrary setting of acquirement periods permits the user to have as many measurements as desired in a day, not limiting the number of the measurement to one for each day as in the prior art. In case that only one measurement is permitted in a day, the measurement can be effected for the acquirement period, which may be so selected that the body fat percentage is relatively stable for the period, compared with other periods for which the body fat percentage is not stable; the significant daily change of body fat percentage would be caused by drinking water, taking an exercise or taking a bath.

If a relatively short length of time is selected as the acquirement period, and even if the measurement is effected wrongly in a registration mode other than that allotted to the user, the acquirement period is so short that the probability with which others' records may be infringed is reduced to minimum.

In the graphic representation 33 or 63 the time-related arrangement of columns may be representative of days, weeks, months, months and days, months and weeks, weeks and days, or months and weeks irrespective of whether such time-related arrangement may be composed of data measured at intervals or without intermission. In this particular embodiment the weight value and the body fat percentage appear alternately, but these values may appear simultaneously in two different locations.

The present invention is described as being applied to a body fat gauge equipped with a weight scale, but it may be equally applied to a body fat gauge, a body water content gauge, a pulse monitor or a BMI gauge, provided that each kind of gauge has a function of providing graphic representations.

As may be understood from the above, the present invention provides following advantages:

the time-related arrangement of rectangles is limited to relatively narrow vertical range in each column, thus facilitating the survey of measured data even if there appear blanks if any, in the graphic representation.

The rectangles of different columns may be changed in shape and/or size and/or color, thereby making different columns distinctively distinguishable from each other, thereby facilitating the time-related survey of measured data still more.

The rectangle representing the measured value beyond the permissible maximum may be changed in appearance, thereby indicating that the measured value is beyond the permissible maximum.

The indication of the unit quantity of each mark-to-mark space or division is given when the permissible maximum measurement range is switched to the permissible minimum measurement range or vice versa. This contributes to the facilitating of quick understanding of the graphic representation.

The acquirement decision making means permits the user to make a required decision, thereby reducing blanks which otherwise, may appear in the graphic representation, and leaving the recording of measured data to his discretion. Also advantageously, records of others' measurements cannot be invaded.

The warning means permits the user to be aware of the measurement using others' personal particulars, thus preventing invasion of the records of others' measurements.

The setting of data-acquirement periods permits the user to make required measurements in pace with his life-way, thus reducing blanks which otherwise, would appear in the graphic representation, and leaving the recording of measured data to the user's discretion. The probability with which others' records are invaded can be reduced to possible minimum.

What is claimed is:

1. A living body variable measuring apparatus equipped with a display capable of presenting a graphic representation characterized in that the graphic representation is composed of a crosswise arrangement of rectangles comprising a vertical column of rectangles in ordinate representing a measured quantity, and a horizontal line of rectangles in abscissa representing time;

wherein the measured quantity in each horizontal line is indicated by only one rectangle among the rectangles of each vertical column; and wherein the rectangular presentation beyond the permitted range of measured quantity is different from the rectangular presentation within the permitted range of measured quantity in appearance.

2. A living body variable measuring apparatus equipped with a display capable of presenting a graphic representation characterized in that the graphic representation is composed of a crosswise arrangement of rectangles comprising a vertical column of rectangles in ordinate representing a measured quantity, and a horizontal line of rectangles in abscissa representing time;

wherein the measured quantity in each horizontal line is indicated by only one rectangle among the rectangles of each vertical column; and wherein the display shows how much a mark-to-mark space indicates when switching from the minimum range of measurement to the maximum range of measurement in the scale.

3. A living body variable measuring apparatus equipped with a display capable of presenting a graphic representation characterized in that the graphic representation is composed of a crosswise arrangement of rectangles comprising a vertical column of rectangles in ordinate representing a measured quantity, and a horizontal line of rectangles in abscissa representing time;

wherein the measured quantity in each horizontal line is indicated by only one rectangle among the rectangles of each vertical column;

further comprising a decision making unit, thereby permitting the user to make a required decision in terms of whether the measured quantity should be recorded or not, said graphic representation being based on the latest measured quantity and a previous measured quantity, the recording of which was decided;

wherein a measured quantity is always indicated in each time-sequential section of the horizontal line.

4. A living body variable measuring apparatus according to claim 3 wherein in case of two or more people being permitted to record their measurement results it further comprises a warning unit which informs the user of wrong measurement if made, by referring to others' particulars already registered.

5. A living body variable measuring apparatus equipped with a display capable of presenting a graphic representation characterized in that the graphic representation is composed of a crosswise arrangement of rectangles comprising a vertical column of rectangles in ordinate representing a measured quantity, and a horizontal line of rectangles in abscissa representing time;

wherein the measured quantity in each horizontal line is indicated by only one rectangle among the rectangles of each vertical column;

further comprising a data-acquirement time setting unit, thereby permitting the user to selectively determine at what time the required measurement may be made, said graphic representation being based on the quantity measured at the time thus set for data-acquirement, wherein a measured quantity is always indicated in each time-sequential section of the horizontal line.

6. A living body variable measuring apparatus equipped with a display capable of presenting a graphic representation characterized in that the graphic representation is composed of a crosswise arrangement of rectangles comprising a vertical column of rectangles in ordinate representing a measured quantity, and a horizontal line of rectangles in abscissa representing time;

wherein the measured quantity in each horizontal line is indicated by only one rectangle among the rectangles of each vertical column; and wherein different lengths of time allotted to different measurements are distinguishable in color.

\* \* \* \* \*